(12) United States Patent
Dorawa et al.

(10) Patent No.: US 8,556,947 B2
(45) Date of Patent: Oct. 15, 2013

(54) DEVICE FOR FIXATION OF BONE FRACTURES

(75) Inventors: Klaus Dorawa, Schönkirchen (DE); Manuel Schwager, Zurich (CH); Christopher Rast, San Diego, CA (US); Marcel Aeschlimann, Ligerz (CH); Philipp Seiler, Arboldswil (CH)

(73) Assignee: Stryker Trauma GmbH (DE)

( * ) Notice: Subject to any disclaimer, the term of this patent is extended or adjusted under 35 U.S.C. 154(b) by 1082 days.

(21) Appl. No.: 11/879,045

(22) Filed: Jul. 13, 2007

(65) Prior Publication Data
US 2009/0018590 A1    Jan. 15, 2009

(51) Int. Cl.
*A61B 17/86* (2006.01)

(52) U.S. Cl.
USPC .......................................... 606/301; 606/304

(58) Field of Classification Search
USPC ......... 606/300, 301, 304, 309, 310, 314, 318, 606/323, 328, 331, 92, 916; 623/23.48, 623/23.58, 17.12; 411/82, 82.1, 82.3, 258, 411/930; 405/259.5
See application file for complete search history.

(56) References Cited

U.S. PATENT DOCUMENTS

| 4,653,489 A | 3/1987 | Tronzo |
| 6,048,343 A * | 4/2000 | Mathis et al. ................. 606/916 |
| 2004/0138672 A1* | 7/2004 | Michelson ...................... 606/99 |
| 2006/0122624 A1 | 6/2006 | Truckai et al. |
| 2007/0260250 A1 | 11/2007 | Wisnewski et al. |

FOREIGN PATENT DOCUMENTS

| JP | 2003-159258 | 6/2003 |
| WO | WO-02/069817 | 9/2002 |
| WO | WO-2004/017857 | 3/2004 |

* cited by examiner

*Primary Examiner* — Michael T Schaper
(74) *Attorney, Agent, or Firm* — Lerner, David, Littenberg, Krumholz & Mentlik, LLP

(57) ABSTRACT

A device and method for fixation of bone fractures has a bone screw comprising a shank with a threaded end portion, on the outer surface. The screw has a through bore with two bore portions differing in diameter. A step in the diameter is formed between these bore portions and is located within the end of the screw having the thread. This step in diameter can support a metal insert which in turn supports a polymer pin when the latter if pressurized with a sonotrode in the bone screw. Together with an applied ultrasonic vibration the pressure fluidizes the polymer pin and presses the material through holes configured in the wall of the bone screw and into surrounding bone.

16 Claims, 3 Drawing Sheets

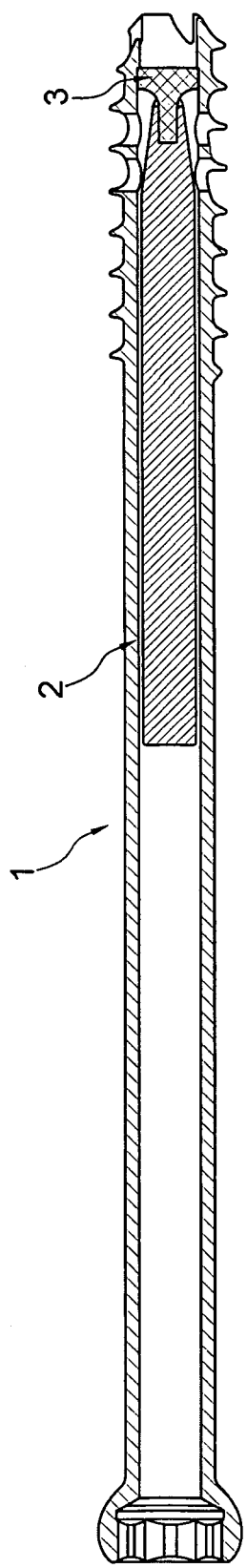
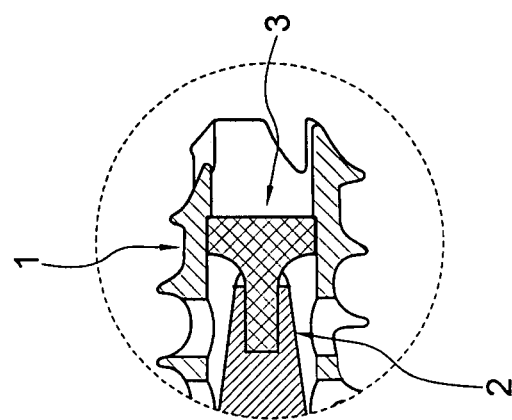

DEVICE FOR FIXATION OF BONE FRACTURES

BACKGROUND OF THE INVENTION

The invention relates in general to sonic fusion technology, it relating more particularly to a device and a method for the fixation of bone fractures, with a bone screw for augmenting within a bone.

Known from U.S. Pat. No. 4,653,489 is a system wherein a fixation cement is introduced through a bone screw into a portion of a bone afflicted by osteoporosis. Femoral neck fractures as well as distal femoral fractures can be fixated by means of this device.

The system in accordance with prior art comprises a bone screw having a flow cavity, i.e. an axial through bore through which bone cement can be introduced into the portion at the tip of the screw. The bone cement is advanced by a device which is releasably attached to the trailing end of the screw. This device is similar to a commercially available syringe in comprising substantially a cylindrical barrel and a plunger. The barrel forms a cavity in which the plunger is movable to and fro.

In use of this prior art device the fixation cement is filled into the barrel, after which the plunger is urged against the cement. By applying manual compression force the fixation cement is jetted into the axial through bore of the bone screw. Due to the pressure the fixation cement is adequately fluidized so that it can pass through the proximal end of the bone screw into the bone, as a result of which the bone screw is augmented in the bone.

This system has the drawback that the manual pressure applied to the fixation cement varies, not only basically from application to application but also during the application itself so that the distribution of the fixation cement within the portion of the bone at the tip of the bone screw is neither reliable nor even.

SUMMARY OF THE INVENTION

An object of the invention is to define a device and a method by means of which a reliable and even augmentation of a bone screw at an implantation site in the bone can now be assured.

An aspect is achieved in accordance with the invention by the bone screw for fixation of a bone fracture, having a bone screw comprising a shank having a first threaded end and having along its longitudinal center line an axial through bore having a first bore portion with a first diameter and a second bore portion with a second diameter, wherein the first diameter is larger than the second diameter and the second bore portion is adjacent the first shank end, and a step in the bore between the first and the second bore portions. Another aspect is achieved by a method for fixation of a bone fracture comprising the steps of screwing a bone screw having an axial bore therein with transverse passageways, connecting the bore with an outer surface of the bone screw into a bone across a fracture site, combining a polymer pin with a metal insert, inserting the polymer pin together with the metal insert into the axial through bore in the bone screw, pressuring and vibrating the polymer pin, wherein the polymer pin is supported by the metal insert which is in turn supported by a step in the diameter in the through bore, resulting in the polymer pin being fluidized at its tip, the fluidized polymer material being pressed out of the bone screw.

The invention will now be detailed by way of a preferred embodiment with reference to the attached drawings in which:

BRIEF DESCRIPTION OF THE DRAWINGS

FIG. 5 is a section view of a device for fixation of a bone fracture in accordance with one embodiment of the invention, with the bone screw as shown in FIG. 1 in which the polymer pin as shown in FIG. 3 and the metal insert as shown in FIGS. 4a, 4b are inserted; and FIG. 6 is a detail view of the tip of the device as shown in FIG. 5.

DETAILED DESCRIPTION

Figure 1:
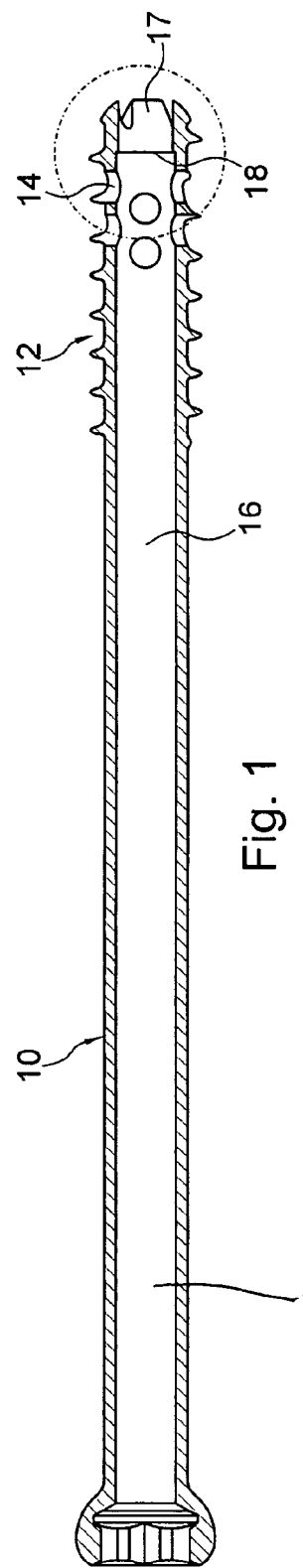
FIG. 1 is a section view of a bone screw in accordance with one embodiment of the invention.

Referring now to FIG. 1 there is illustrated a bone screw 10 in accordance with the invention. The bone screw comprises a shank and a thread 12 machined in an end portion of the shank, although the thread may also cover the shank of the screw full length. In addition, the bone screw 10 is cannulated. The cannulation is provided along the longitudinal center line of the screw as a through bore 11 composed of two bore portions 16, 17. Bore portion 16 comprises a first diameter and bore portion 17 a second diameter, the first diameter being larger than the second diameter. In addition the bore portion 16 forms the main portion of through bore 11. In the preferred embodiment, just a small portion adjoining the end of the shank of the bone screw in which the thread 12 is machined is formed by the bore portion 17. The transition from the bore portion 16 to the bore portion 17 is formed by a step 18 in the bore 11. The step 18 in the bore forms an annular ridge having substantially right-angled edges at the wall of the through bore within the bone screw. The edges of the step 18 in the diameter may be machined flat or rounded. The screw features transverse holes 14 which extend through the wall of the bore portion 16 to allow polymeric material within the bore 11 to flow out of bore 11 and into the adjacent bore. Furthermore the position of the step in diameter together with the holes in the wall can be positioned optionally along the longitudinal center line and thus the location of the polymeric augmentation can be determined in accordance with the particular application and the desired effect.

In the preferred embodiment the holes 14 may be configured in differing directions perpendicular to the longitudinal center line of the bone screw and arranged in the end portion with the thread 12. Preferably the holes 14 are arranged in a region of the end portion which also features the bore portion 16. In the embodiment as shown in FIG. 1 two holes 14 each are configured axially juxtaposed in the bore portion 16 and through the thread 12. Furthermore, four such pairs of holes are evenly distributed about the circumference of the bone screw, in other words, circumferentially spaced by 90°. It is, however, just as possible that three, four, five or more holes may be provided circumferentially and it is not necessary that the holes circumferentially distributed are all at same axial level. Apart from this, transverse or longitudinal oblong holes, slots, or the like may be provided.

Figure 2:
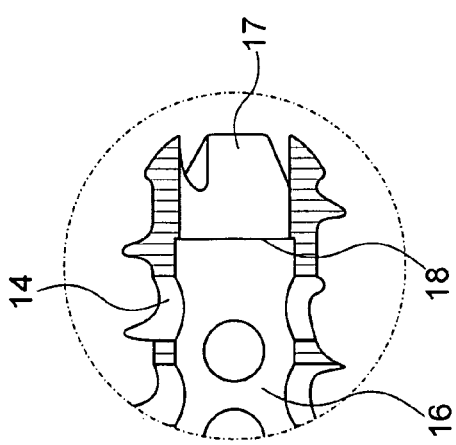
FIG. 2 is a detail view of the tip of the bone screw as shown in FIG. 1.

Referring now to FIG. 2 there is illustrated the tip of the bone screw as shown in FIG. 1 but on a magnified scale, the step 18 in the diameter between the bore portion 16 and bore portion 17 now being particularly evident. Apart from this, a few of the holes 14 are shown which are configured passing through the thread 12 in the bore portion 16.

Figure 3:
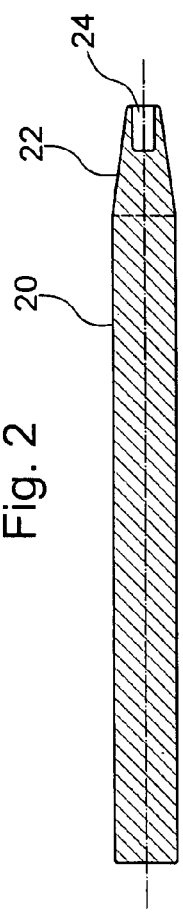
FIG. 3 is a view of a polymer pin in accordance with one embodiment of the invention.

Referring now to FIG. 3 there is illustrated a polymer pin 20 elongated in shape and slightly tapered at a conically tapered end 22. Provided in the conically tapered end 22 of the polymer pin 20 is a concavity or counterbore 24 in the end face. The polymer pin 20 may also be made of other materials such as for instance a thermoplastic material suitable for augmenting a bone screw, both resorptive and non-resorptive materials being useful.

Figure 4A:
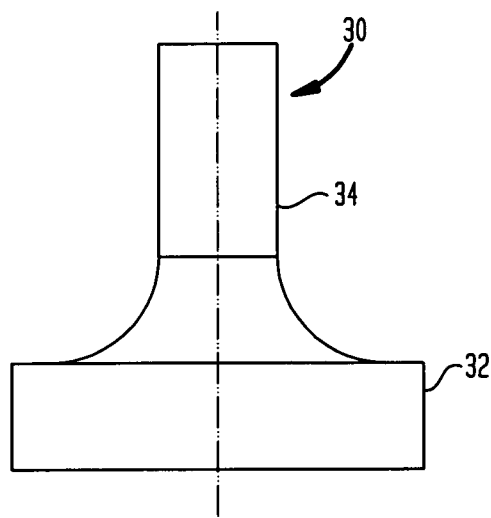
FIGS. 4a and 4b are a side view and respectively a plan view of a metal insert in accordance with one embodiment of the invention.
Figure 4C:
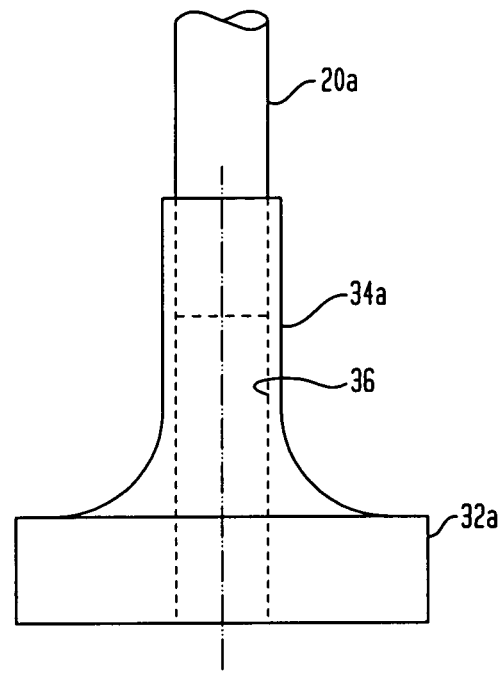
FIG. 4c is an elevation view of an alternate embodiment showing the connection of a polymer pin and a metal insert.
Figure 4B:
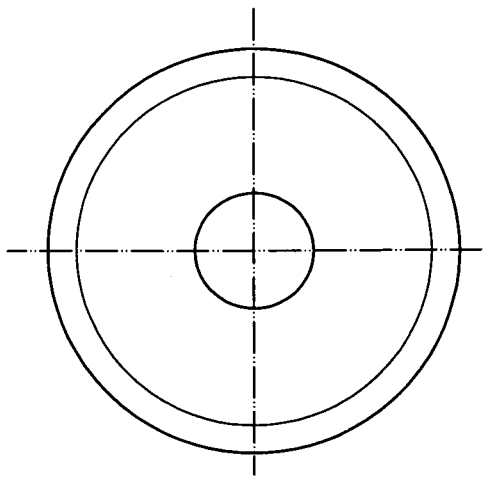
Figure 4D:
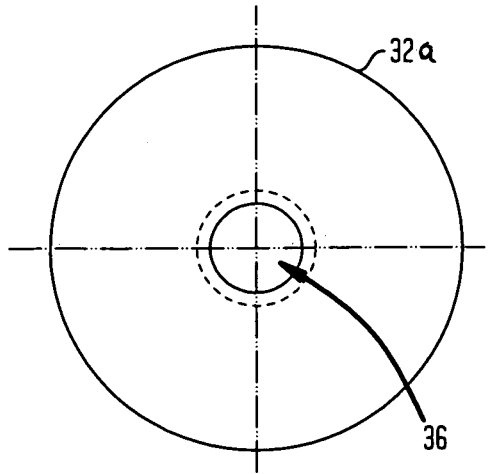
FIG. 4d is a bottom view of the embodiment of FIG. 4c.

Referring now to FIGS. 4a and 4b a metal insert is shown in a side view and in a plan view. The metal insert features a substantially disk-shaped end 32 and a substantially pin-shaped end 34. The disk-shaped end 32 has an outer diameter somewhat smaller than the diameter of the bore portion 16 and somewhat larger than the diameter of the bore portion 17. The pin-shaped end 34 is configured so that it can be inserted into the counterbore in the polymer pin.

In another embodiment (not shown) the metal insert features instead of the pin-shaped end 34 a protruding end suitable for snap mounting, the polymer pin in this case having a snap mounting end corresponding to the protruding end. When the metal insert is snap mounted with the polymer pin, both elements can be inserted together into the bone screw, it being of advantage when the snap mount comprises a slight clearance when connected. This clearance has the advantage that when the polymer pin is pressurized it can be better fluidized at the joint with the metal insert to thus easier jet from the bone screw into the bone.

It is furthermore possible that a metal insert 32a instead of featuring a protruding or pin-shaped end has a protruding end 34a with a through bore 36 into which a corresponding end of the polymer pin 20a can engage. In this embodiment the polymer material is jetted axially from the bone screw not only through the holes 14 but also out the leading end of the screw through the hole in the metal insert. the proportion of the polymer material emerging from the holes and bores can be varied by the size thereof.

Depending on the aspect concerned, a snap mount may also be provided in combination with axial and/or radial holes, it being just as possible, however, to configure the metal insert integrally with the bone screw. In this arrangement the step in the diameter between two portions of the bore is configured by a larger difference in diameter; indeed, even an axial blind hole may be used on the cannulation instead of the full axial through bore in the bone screw.

The following details inserting the bone screw into a bone. Firstly a K wire is powered up to the site in a bone at which the bone screw is to be located. Via the K wire the bone screw is then advanced and ultimately screwed into place until it is sited as desired. After insertion of the bone screw in the bone the K wire is removed. This procedure makes it necessary that the bone screw features a full length through bore. This is a popular operation technique because the operator can best check the position of the screw. The K wire is also used to measure the necessary screw length.

After removal of the K wire the passageway or through bore 11 along the longitudinal center line of the bone screw is free to receive polymer pin 20 together with metal insert 30. Tip 34 of the pin shaped end of metal 30 insert is inserted into counterbore 24 of polymer pin 20. Referring now to FIG. 5 there is illustrated how metal insert 30 rests on the step formed by the step 18 in the bore when polymer pin 20 with the metal insert 30 has been inserted facing the direction of the tip. It is in this way that the step 18 in the diameter forms within the bone screw a counterhold for the metal insert which in turn supports the polymer pin when the polymer pin is pressurized and vibrated by an ultrasonic handpiece/sonotrode which, for this purpose, is mounted on the free end of the bone screw. The vibration and pressure generated by the ultrasonic handpiece and applied to the polymer pin fluidizes the polymer pin so that the material of the polymer pin emerges from the radially arranged holes 14 into the bone. It is in this way that the polymer pin furnishes the material for augmenting the bone screw in the bone.

It is to be noted that the present invention is not just limited to the indications as recited above. In other words, all screw applications which can be supplied by cannulated screws can be potentially supplied with the option of polymeric fastening and thus with the device in accordance with the invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for fixation of a bone fracture by use of ultrasonic energy, comprising:
   a bone screw comprising a shank having a first threaded end portion and having along its longitudinal center line an axial through bore having a first bore portion with a first diameter and a second bore portion with a second diameter, wherein the first diameter is larger than the second diameter and the second bore portion is adjacent the first threaded end portion, and a step in the bore between the first and the second bore portions;
   a metal insert having a disk-shaped first end having a diameter smaller than the first diameter and larger than the second diameter, the metal insert having a second end having a diameter smaller than the diameter of the first end of the metal insert; and
   a polymer pin for insertion into the first bore portion of the bone screw with the first diameter, the polymer pin having a leading end with a recessed bore for receiving the second end of the metal insert, the recessed bore having an end wall defining a base of the recessed bore, the metal insert second end having an end face contacting the end wall of the base of the recessed bore for the transmission of ultrasonic energy from the metal insert to the leading end of the polymer pin for fluidizing the leading end.

2. The device as set forth in claim 1, wherein the shank has a non-threaded portion and the step in the through bore is located in the threaded end portion.

3. The device as set forth in claim 1 wherein the bone screw further comprises holes in a wall of the bore of the bone screw, the holes are located in the threaded end portion adjacent the step in the bore.

4. The device as set forth in claim 1 wherein the metal insert is dimensioned so that the first end rests on the step in the bore when the metal insert is inserted into the bore in the bone screw, and wherein the leading end of the polymer pin is configured so that it is insertable into the through bore.

5. The device as set forth in claim 1 wherein the disk-shaped first end is dimensioned so that it rests on the step in the bore when the metal insert is inserted into the bone screw bore and the second end has a pin-shaped portion, and wherein the recessed bore is a counterbore that is configured to receive the pin-shaped portion on the metal insert with which it is connectable.

6. The device as set forth in claim 1 wherein the polymer pin leading end has a radially inwardly tapered outer surface.

7. The device as set forth in claim 1 wherein the polymer pin has a diameter less than the diameter of the first bore portion to thereby form a gap therearound.

8. A device for fixation of a bone fracture using ultrasonic energy, comprising
   a bone screw having a shank with a first threaded end and having along a longitudinal center line thereof an axial through bore having a first bore portion with a first diameter and a second bore portion with a second diameter, wherein the first diameter is larger than the second diameter and the second bore portion is adjacent the first threaded end, and a step is formed in the bore between the first and the second bore portions;
   a metal insert, and
   a polymer pin having a first end for insertion into the first bore portion of the bone screw, wherein the metal insert comprises a substantially disk-shaped first end dimensioned for resting on the step in the bore when the metal insert is inserted into the bone screw first bore portion and has a second end including a pin-shaped portion, and wherein the polymer pin first end has a counter bore configured to receive the second end pin-shaped portion on the metal insert with which it is connectable, for the transmission of ultrasonic energy from the metal insert to the first end of the polymeric pin.

9. The device as set forth in claim 8 wherein the metal insert is dimensioned so that its first end rests on the step in the bore when the metal insert is inserted into the first bore portion in the bone screw, and wherein the first end of the polymer pin is configured so that it is insertable into the first bore portion.

10. The device as set forth in claim 8 wherein the polymer pin first end has a radially inwardly tapered outer surface.

11. A device for fixation of a bone fracture using ultrasonic energy, comprising
    a bone screw having a shank with a first threaded end and having along its longitudinal center line an axial through bore having a first bore portion with a first diameter and a second bore portion with a second diameter, wherein the first diameter is larger than the second diameter and the second bore portion is adjacent the first threaded end, and a step in the bore between the first and the second bore portions,
    a metal insert and
    a polymer pin for insertion into the bore of the bone screw, wherein the metal insert has a substantially disk-shaped first end and dimensioned so that it can rest on the step in the bore when the metal insert is inserted into the bore of the bone screw, the metal insert having a second end, and wherein a first end of the polymer pin has a recess having a bottom surface, the recess corresponding in diameter to the second end of the metal insert for receiving the same, the metal insert capable of transferring ultrasonic energy to the first end of the polymer pin.

12. The device as set forth in claim 11 wherein the disk-shaped first end is dimensioned so that it rests on the step in the bore when the metal insert is inserted into the bone screw bore and the second end has a pin-shaped portion, and wherein the recess in the polymer pin is a counterbore configured to receive the pin-shaped portion on the metal insert with which it is connectable.

13. The device as set forth in claim 11 wherein the polymer pin has a diameter less than the diameter of the first bore portion to thereby form a gap therearound.

14. A device for fixation of a bone fracture using ultrasonic energy, comprising
    a bone screw having a shank with a first threaded end and having along its longitudinal center line an axial through bore having a first bore portion with a first diameter and a second bore portion with a second diameter, wherein the first diameter is larger than the second diameter and the second bore portion is adjacent the first threaded end portion, and a step in the bore between the first and the second bore portions;
    a metal insert; and a polymer pin for insertion into the bore of the bone screw, wherein the metal insert has a substantially disk-shaped first end dimensioned so that the first end rests on the step in the bore when the metal insert is inserted into the bore in the bone screw, and the metal insert has an axially extending coupling element at a second end, and wherein a first end of the polymer pin is configured so that it can engage the axially extending coupling element at the second end of the metal insert along its axial extent for the transmission of ultrasonic energy from the metal insert to the first end of the polymer pin.

15. The device as set forth in claim 14, wherein the bone screw shank has a non-threaded portion and the step in the through bore is located in the threaded end portion.

16. The device as set forth in claim 14, wherein the bone screw further comprises holes in a wall of the bore of the bone screw, the holes are located adjacent the step in the bore.

\* \* \* \* \*